United States Patent [19]

Salmon et al.

[11] Patent Number: 5,529,060
[45] Date of Patent: Jun. 25, 1996

[54] HUMIDIFIERS WITH CONTROL SYSTEMS TO PREVENT CONDENSATION

[75] Inventors: Andrew P. M. Salmon; David P. Stewart; Michael G. Daniell, all of Auckland, New Zealand

[73] Assignee: Fisher & Paykel Limited, Auckland, New Zealand

[21] Appl. No.: 272,943

[22] Filed: Jul. 11, 1994

Related U.S. Application Data

[63] Continuation of Ser. No. 887,694, May 22, 1992, abandoned.

[30] Foreign Application Priority Data

May 22, 1991 [NZ] New Zealand ............... 238225

[51] Int. Cl.$^6$ .................... A61M 15/00; A61M 16/10; H05B 3/1
[52] U.S. Cl. ................. 128/203.16; 128/203.17; 128/203.27
[58] Field of Search ............ 128/203.12, 203.16, 128/203.17, 203.26, 203.27, 204.14, 204.17

[56] References Cited

U.S. PATENT DOCUMENTS

| | | | |
|---|---|---|---|
| 4,621,632 | 11/1986 | Bartels et al. | 128/203.27 |
| 4,647,218 | 3/1987 | Figler et al. | 128/204.17 |
| 4,682,010 | 7/1987 | Drapeau et al. | 128/204.17 |

FOREIGN PATENT DOCUMENTS 2130401  5/1984  United Kingdom ............ 128/204.17

*Primary Examiner*—Kimberly L. Asher
*Attorney, Agent, or Firm*—Trexler, Bushnell, Giangiorgi & Blackstone, Ltd.

[57] ABSTRACT

A humidifier in which the temperature of the humidified gases leaving the humidifying chamber of the humidifier is measured. The measured temperature is compared with a predetermined temperature required for a minimum humidity level for humidified gases supplied to a patient and if the measured temperature is less from the predetermined temperature a warning is provided. The humidifier also has a securing device for securing the humidifying chamber to the heater plate of the humidifier. The securing device comprises a sprung gate member which is biased in an upward position to prevent the humidifying chamber from being removed but may be pressed downwardly by a user in order to engage or remove the chamber.

8 Claims, 4 Drawing Sheets

HUMIDIFIERS WITH CONTROL SYSTEMS TO PREVENT CONDENSATION

This is a continuation of application Ser. No. 07/887,694 filed on May 22, 1992, now abandoned.

BACKGROUND OF THE INVENTION (1) Field of Invention

This invention relates to humidifiers of the type for use in providing humidified gases to a patient in a hospital in need of such humidified gases. The invention has been devised particularly though not solely for providing methods of and/or apparatus for providing an indication as to when the humidity of a humidified gas or gases supplied by a humidifier of the type described is unacceptably low in many applications, and for providing methods of and/or apparatus for removably securing a humidifying chamber to humidifying apparatus.

(2) Prior Art

Humidifiers for supplying humidified gas to a patient, eg. a hospitalised patient are known. A humidifier of this type which includes a humidifying chamber is described in the specification of our U.S. Pat. No. 4,203,027. One of the problems associated with humidifiers of this type is that humidified gases are supplied some distance through gas conduits from the humidifying chamber to the patient, which causes the humidified gases to cool before reaching the patient Such cooling reduces the humidity of the gases and condensation will often form on the inner walls of the conduit. In order to help prevent such cooling, heating elements may be provided within the humidified gases conduit. However, care must be taken not to maintain the humidified gases at too high a temperature when supplied to the patient, since gases at high temperatures will cause burns or at least make the patient uncomfortable.

Humidifiers of the type which have a humidifying chamber which slides on to a base such as a heater plate of the humidifier are also disclosed in the specification of our U.S. Pat. No. 4,203,027. Although such a sliding action facilitates placing the humidifying chamber on the heater plate of a humidifier, it is also relatively easy for the humidifying chamber to be dislodged from the heater plate, preventing operation of the apparatus.

BRIEF SUMMARY OF THE INVENTION

It is an object of the present invention to provide methods and/or apparatus of the type described which will overcome the foregoing disadvantages.

Accordingly, the invention may be said to consist in a method of monitoring the temperature of a humidified gas or gases supplied by a humidifier of the type for use in providing humidified gases to a patient to provide an indication as to when the humidity of said gases is below a minimum desired level of humidity. The invention uses humidifying apparatus including a humidifying chamber having a gases inlet and a gases outlet, and humidifier chamber heating means to heat, and humidifying means to humidify the gases in the chamber. A conduit connected to the gases outlet conveys humidified gases to a patient at a remote destination and conduit gas heating means within the conduit heat the humidified gases being supplied. Destination temperature selection means for selecting a destination temperature of said humidified gases at said destination are provided, together with conduit temperature selection means for selecting a difference temperature, being the difference in temperature of humidified gases between the outlet and the destination. Processor means are also provided for determining when the humidity of the humidified gases is below the minimum desired level. The method of the invention comprises the steps of algebraically adding the destination temperature to the difference temperature with the processor means to determine the temperature of the humidified gases at the outlet, comparing the temperature of the humidified gases at the outlet with a temperature corresponding to the minimum desired level of humidity, and providing a low humidity indication if the outlet temperature is less than the desired temperature.

To those skilled in the an to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples only.

DETAILED DESCRIPTION OF THE PREFERRED EMBODIMENT

Figure 1:
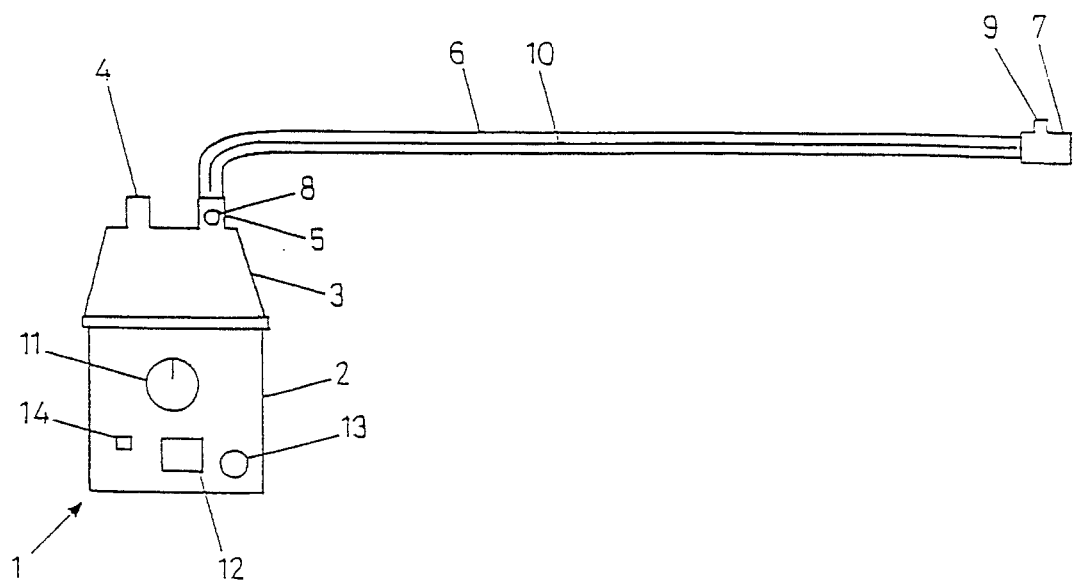
FIG. 1 is a diagrammatic sketch of humidifying apparatus in accordance with the present invention.

Referring to FIG. 1, a humidifying apparatus generally referenced 1 is shown. The apparatus comprises a body 2 containing heating means comprising heating apparatus, for example, a heating element and processor means for calculating temperature differences to indicate humidity. Control means are also provided within the body 2 for controlling the temperatures of humidified gases supplied by the humidifying apparatus. The body 2 is in engagement with a humidifying chamber 3 which contains water for humidifying gases, for example, a mixture of air, oxygen and anaesthetic within the chamber. The chamber also has a gases inlet 4 and a gases outlet 5, the gases outlet 5 being connected to the conduit 6 which conveys humidified gases to a remote destination, for example, an intubated patient at the end 7 of the conduit. The humidifier chamber outlet 5 has a temperature transducer 8 comprising for example, a thermistor. Transducer 8 is in connection with a processor means comprising a microcomputer, for example, which includes an input/output port and a microprocessor and associated memory in body 2 of the apparatus. The control means monitors the temperature recorded at the gases outlet 8, and the heating element within the apparatus is controlled by the control means to supply the required amount of heat so that the humidified gases passing through outlet 5 and about the transducer 8 are kept to the temperature required by a user. Similarly, a further temperature transducer 9 comprising, for example, a thermistor is provided at end 7 of the conduit and this temperature transducer is also in connection with control means which monitor the temperature of the humidified gases in the end of the conduit. The control means supply heat to a heating element 10 within the conduit if the temperature at end 7 of the conduit is not sufficiently high. If the temperature is higher at end 7 than that temperature selected by a user then energy is not supplied to the heating element 10 and the natural cooling effect of the conduit relied upon to lower the temperature towards the user selected temperature if required. The temperature data supplied by the thermistors 8 and 9 may be in analogue form, being convened to digital form by the microcomputer or before input to the microcomputer.

The desired temperature at the end 7 of the conduit, and thus the temperature of the gases supplied to the patient is selected by a user using destination temperature selection means comprising a dial 11. The dial 11 is rotated to indicate a destination temperature and the destination temperature is also displayed on a display, for example, a liquid crystal display or a light emitting diode display 12 on the front panel of the humidifying apparatus.

A conduit temperature selection means comprising a dial 13 on the humidifying apparatus is also provided and is used to select a difference temperature, being the difference in temperature of the humidified gases between end 7 of the conduit 6 and the gases outlet 5 from the humidified chamber. Thus, once the desired temperature of humidified gases at end 7 has been selected, the selection of the difference temperature using dial 13 will effectively select the temperature of the humidified gases at the gases outlet 5.

The heating element 10 is provided in the conduit 6 to help prevent the humidified gases from cooling and condensing in the conduit as they are conveyed to the remote destination. Heat will generally need to be added to the gases to prevent condensation and the amount of heat the user adds to prevent condensation is determined by the conduit temperature selection means.

The temperature of the gases at the outlet 5 from the humidifying chamber is very important since it is this temperature which determines the absolute humidity of the gases leaving the humidifying chamber. A given temperature of humidified gases corresponds to a certain physically possible maximum humidity of the gases. It has been recognised that the minimum level of humidity necessary in humidified gases, for example air, supplied to intubated patients is approximately 30 milligrams of water per litre of gas. The minimum gases temperature required for this level of humidity is approximately 31° C. Thus the temperature of the humidified gases leaving the outlet 5 of the humidifying chamber should be at least 31° C. for effective operation.

In order to indicate to a user, being an operator of the apparatus, when this desired minimum level of humidity is not being attained, the humidifying apparatus in accordance with the present invention performs the following steps. The processor means comprising, for example, a microprocessor or microcomputer within the body 2 of the humidifying apparatus algebraically adds the temperature selected using dial 11 to the conduit difference temperature selected using dial 13. The result of this addition indicates the selected temperature of the humidified gases leaving the chamber through outlet 5. The temperature of the humidified gases at the outlet 5, outlet 7 is then compared with the minimum required temperature of 31° C. If the temperature is selected so that the temperature at outlet 5, outlet 7 is less than 31° C., then a warning light 14 indicates this situation at the front panel of the apparatus. Other indications may also be provided, for example, an audible alarm or a message displayed on the display 12. During operation of the apparatus, a user enters a selected Destination Temperature (temperature at which the user would like the gases leaving the conduit to be at) and a Difference Temperature (the change in temperature which the user would like between the gases leaving the humidifier and the gases being supplied at the patient end of the conduit) to the processor means. A negative value for the Difference Temperature indicates that the heating element 10 within the conduit will be required to be activated to increase the temperature of the gases although it should be noted that the difference temperature could be positive or negative in value. The processor means then determines the temperature of the gases leaving the gases outlet 8 of the humidifier by algebraically adding the Difference Temperature to the Destination Temperature.

The following table presents specific example values of user selected and controller generated temperatures which may arise during operation of the humidifying apparatus according to the present invention.

| User Selected Destination Temperature | User Selected Difference Temperature | Indirectly user selected Outlet Temperature | Alarm raised? |
| --- | --- | --- | --- |
| 28° C. | +5° C. | 33° C. | YES |
| 30° C. | +2° C. | 32° C. | YES |
| 32° C. | −2° C. | 30° C. | YES |
| 33° C. | +2° C. | 35° C. | NO |
| 34° C. | −2° C. | 32° C. | NO |

In the above table, special attention is dram to row 3 in which, although the user selected Destination Temperature is greater than the minimum required temperature (in the case 31° C.), the alarm is still raised because the outlet temperature has been calculated to be less than 31° C. This is due to the obvious fact that the humidity of the gases as they travel through the conduit can not increase and, therefore, if the humidity level of the gases leaving the humidifier is insufficient (that is, less than 31° C.), then no matter what temperature the gases are raised to through the conduit, the humidity level will not reach the required 30 mg $H_2O/L$ Of gas.

Figure 2:
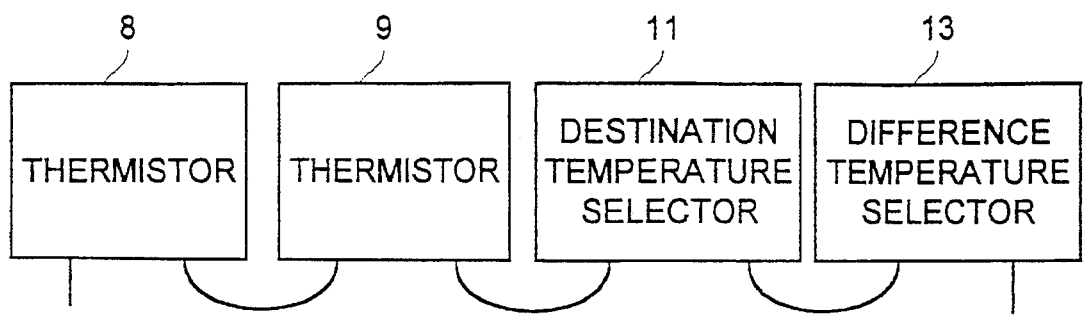
FIG. 2 is a diagrammatic view of a microcomputer and devices associated therewith in accordance with the present invention.
Figure 2:
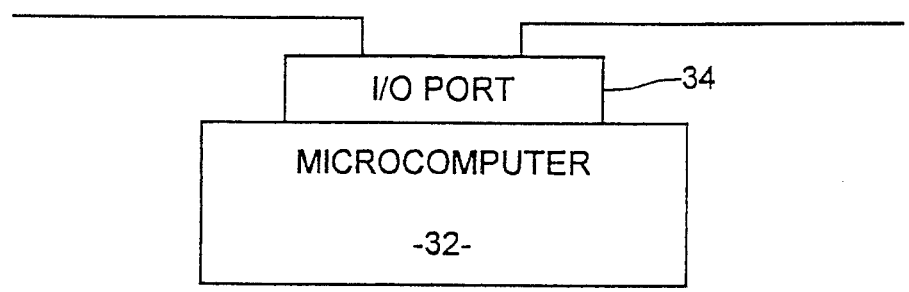

Referring to FIG. 2, a diagrammatic view of a microcomputer 32 including, for example, an Intel 8085 microprocessor used to control the apparatus of the present invention is shown together with diagrammatic views of the devices which supply data to the Input/Output (I/O) port 34 of the microcomputer via a bus 36. The thermistors, being the temperature transducers 8 and 9 of FIG. 1 supply data in either a digital form to I/O Port 34 or in analague form to an analague to digital converter or another port (not shown) of the microcomputer. Similarly, the destination and difference temperature selectors 11 and 13 may also supply data to the microcomputer in digital or analague form. In the preferred embodiment, the thermistors and temperature selectors supply data in analague form to an input of the microcomputer. The analague information is sampled and converted by the microprocessor into digital form for use in controlling the apparatus. When a warning that the temperature at outlet 5 is too low is required, this is provided to a warning light and/or aural indicator, for example a speaker, by the microcomputer sending out an appropriate signal pattern through I/O Port 34 onto bus 36.

Figure 3:
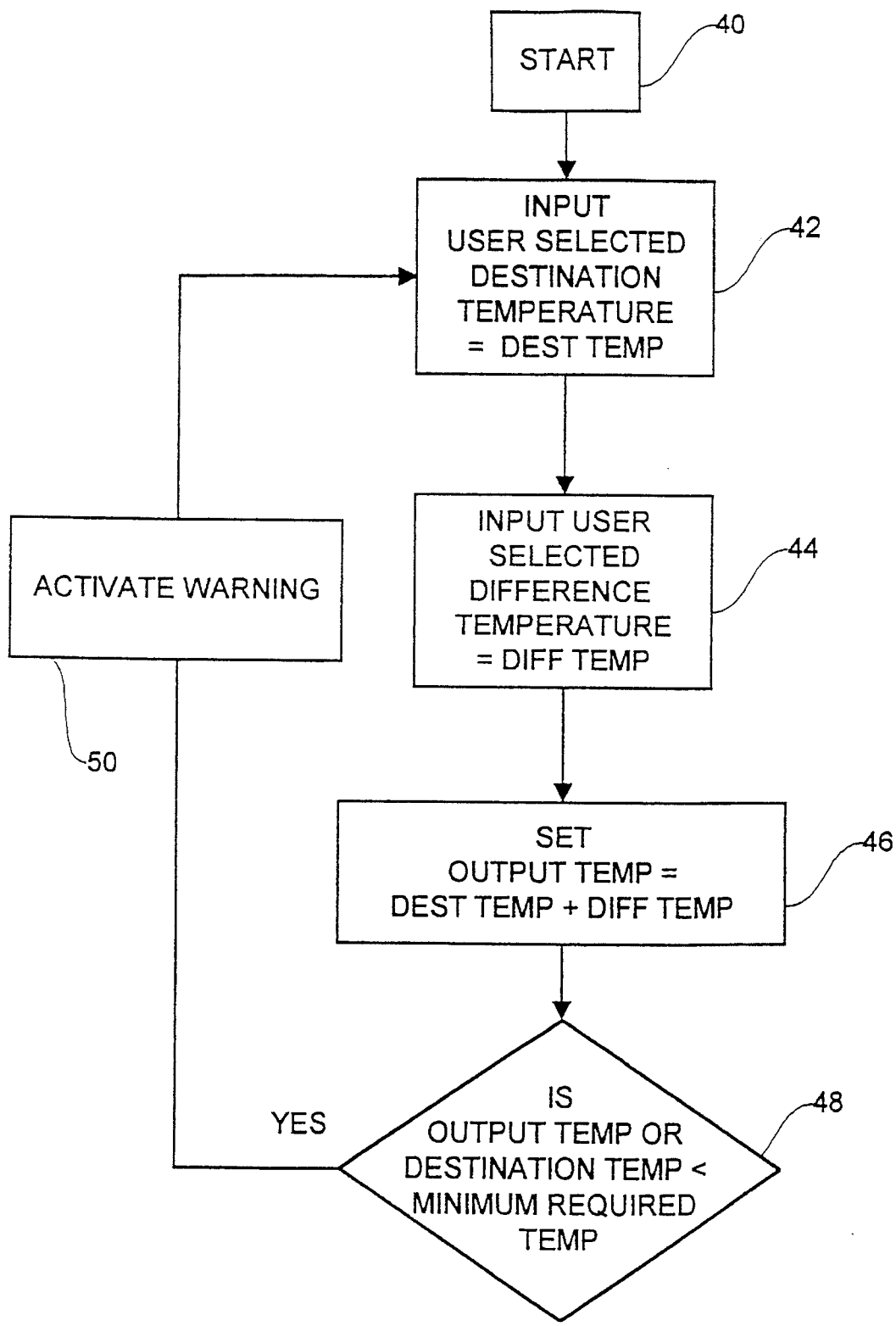
FIG. 3 is a flow chart relating to a computer program used in accordance with the present invention.

The algorithm used by the program in the microcomputer to indicate when the desired minimum level of humidity is not being obtained, is diagrammatically illustrated by the flow chart of FIG. 3.

Referring to FIG. 3, the algorithm begins at start block 40. The selected destination temperature DEST TEMP is sampled at block 42 and the difference temperature (DIFF TEMP) is sampled in block In block 46 the processor means algebraically adds the destination temperature to the difference temperature to obtain the temperature of the gases at outlet 5 (OUTPUT TEMP). The OUTPUT TEMP is compared with the desired temperature (for example 31° C.) in block 48 and if the output temperature is less than the desired temperature a warning is actuated in block 50. The warning is actuated until the difference temperature or the destination temperature is changed so that the output temperature is greater than or equal to the desired temperature.

Figure 4:
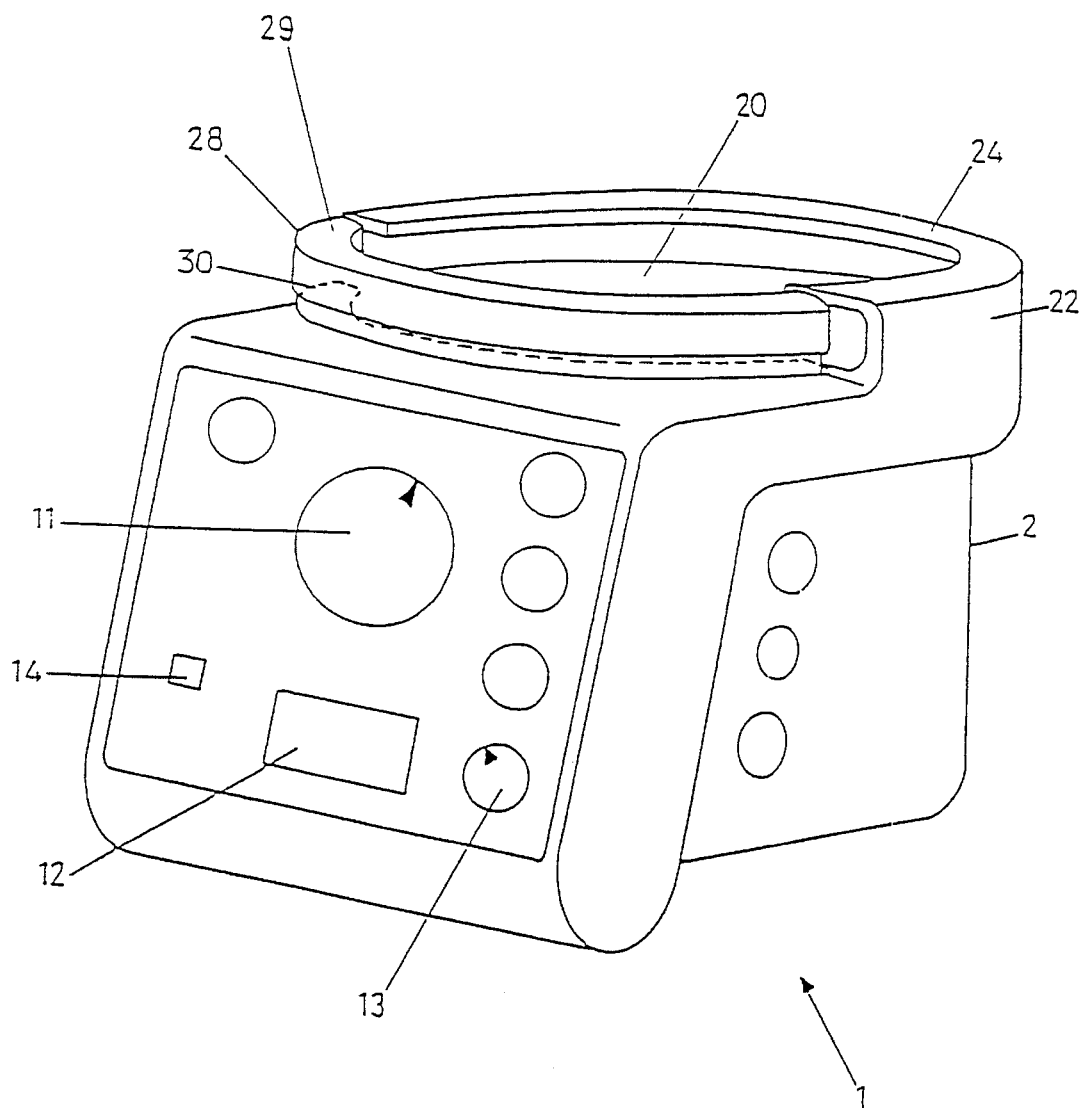
FIG. 4 is a perspective sketch of humidifying apparatus in accordance with the present invention.

Referring now to FIG. 4, the body 2 including the heating apparatus of the humidifying apparatus is shown in more detail. The selection means 11 and 13 are again shown together with display 12 and warning indication 14. The humidifying chamber 3 is in use placed on the upper surface 20 of apparatus 2 and the upper surface 20 comprises a hot plate including the humidifier heating means, for example, a heating element, so that when the base of the chamber 3 is placed on surface 20, water in the humidifying chamber is heated to evaporate the water and thus humidify gases in the chamber. The heating means is controlled by control means in the apparatus 2 to achieve the desired chamber outlet temperature selected by a user. About the outer edges of surface 20 humidifying chamber engagement means are provided comprising wall 22 and flange 24 which is dependent therefrom.

Figure 5:
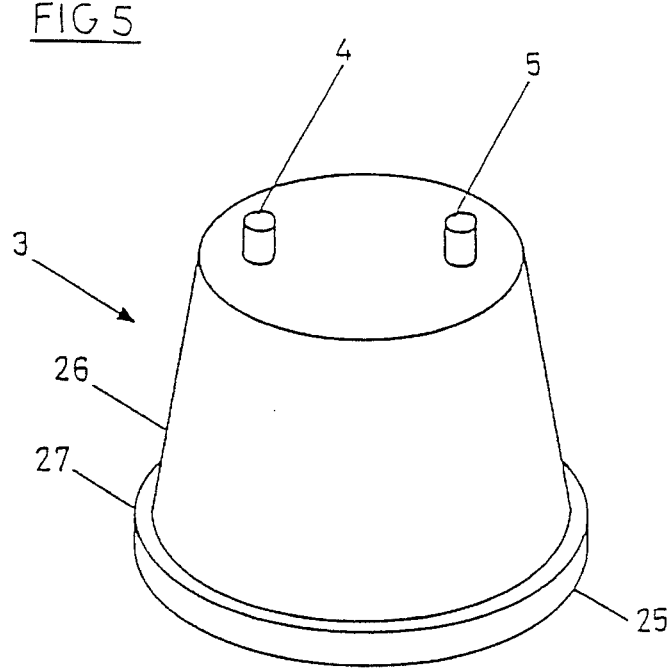
FIG. 5 is a perspective sketch of a humidifying chamber (not to scale) for use with the apparatus of FIG. 4.

Referring now to FIG. 5 a sketch of a humidifying chamber is shown, the chamber having a base 25 and walls 26 and the lower portion of the walls having a shoulder 27 which extends outwardly therefrom. Shoulder 27 comprises heating apparatus engagement means. The heating apparatus 2 also has a gate member 28 comprising an elongate semi-circular member which may be disposed in two positions, upper position as shown in FIG. 4, or a lower position in which the member is forced downwardly so that the upper surface 29 of the gate member is almost level with surface 20 as shown by dashed line 30 in FIG. 4. Thus in use, when a user wishes to place a humidifying chamber such as chamber 3 on the upper surface 20 of heating apparatus 2, the user will either depress gate member 28 by pressing on the upper surface 29 thereof with, for example, a finger, or will place part of the base 25 of the humidifying chamber on the upper surface 29 of the gate member to depress the gate member, then slide the humidifying chamber across the surface 29 of the gate member and on to surface 20 of the heating apparatus. The humidifying chamber is slidably moved a sufficient distance across the surface 20 so that the shoulder 27 on the humidifying chamber engages the walls 22 and flange 24 of the heating apparatus and the shoulder will fit within the recess formed between walls 22 and flange 24. When the humidifying chamber is so engaged the gate member 28 will return to the position shown in FIG. 4 since it is biased in the upward position by a spring, for example. The gate member 28 will return to the upper position either automatically, when the base 25 of the humidifying chamber is contacting only surface 20 and is no longer in contact with surface 29 of the gate member, or when a user removes a finger, for example, from the surface 29 of gate member 28.

Similarly, when a user wishes to remove the humidifying chamber from the heating apparatus the user will again depress gate member 28 by, for example, pressing a finger down on surface 29 to oppose the biasing means so that the gate member is forced into the lower position and the humidifying chamber is removed by sliding the humidifying chamber back across surface 20 and removing it from the engagement means. Once the humidifying chamber has been removed the user allows the gate member to return to the upper biased position as shown in FIG. 4.

It will be seen from the foregoing that a humidifier is provided which provides an indication of undesirably low humidity provided by a humidifier in response to temperature settings selected by a user, and also provides methods and apparatus for removably securing a humidifying chamber to heating apparatus of a humidifier.

We claim:

1. A method of monitoring and controlling a humidifier system comprising the steps of:

i) providing a humidifier system including a humidifying chamber; a gas inlet; a gas outlet; means for heating gas in said humidifying chamber; means for humidifying gas in said humidifying chamber; a patient attachment; a gas conduit connecting said gas outlet to said patient attachment; means for heating gas in said conduit; means for assessing a required minimum temperature at said gas outlet necessary for maintaining a minimum desired humidity level; means for selecting a destination temperature at said patient attachment; means for selecting a difference temperature in said conduit; and an electronic processor unit having algebraic addition capability;

ii) selecting a minimum required gas temperature at said gas outlet necessary to maintain a desired humidity level in gas delivered to a patient;

iii) having a user select a desired destination temperature via said means for selecting a destination temperature;

iv) having a user directly select a difference temperature via said means for selecting a difference temperature and thereby indirectly select the temperature of gas coming out of said gas outlet, said difference temperature being the temperature gas found in said conduit between said gas outlet and said patient attachment is changed by said means for heating gas in said conduit;

v) algebraically adding said selected destination temperature to said selected difference temperature by said electronic processor unit and generating a gas outlet temperature;

vi) comparing said generated gas outlet temperature and said destination temperature to said minimum required gas temperature at said gas outlet;

vii) generating a low humidity signal if said generated gas outlet temperature or said destination temperature is less than said minimum required gas temperature at said gas outlet; and viii) continuously generating said low humidity signal until a user changes said selected destination temperature and/or said selected difference temperature, such that said generated gas outlet temperature and said destination temperature is greater than or equal to said minimum required gas temperature at said gas outlet.

2. A method of monitoring and controlling a humidifier system as claimed in claim 1 wherein said minimum required gas temperature at said gas outlet necessary to maintain a desired humidity level in gas delivered to a patient is a constant and wherein said method further includes the steps of providing said electronic processor unit with memory means and storing said minimum required gas temperature in said memory means.

3. A method of monitoring and controlling a humidifier system as claimed in claim 2 further including the step of providing said electronic processor unit with a warning light and/or aural signal indication means activated by said low humidity signal.

4. A method of monitoring and controlling a humidifier system as claimed in claim 1 further including the step of providing said electronic processor unit with a warning light and/or aural signal indication means activated by said low humidity signal.

5. A humidifier system comprising a humidifying chamber; a gas inlet; a gas outlet; means for heating gas in said humidifying chamber; means for humidifying gas in said humidifying chamber; a patient attachment; a gas conduit connecting said gas outlet to said patient attachment; means for heating gas in said conduit; means for assessing a required minimum temperature at said gas outlet necessary for maintaining a minimum desired humidity level; means for selecting a destination temperature at said patient attachment via which a user selects a desired destination temperature; means for selecting a difference temperature in said conduit via which a user directly selects a difference temperature and thereby indirectly selects the temperature coming out of said gas outlet, said difference temperature being the temperature gas found in said conduit between said gas outlet and said patient attachment is changed by said means for heating gas in said conduit; and an electronic processor unit having algebraic addition capability and storing a program which causes the electronic processor to:

select a minimum required gas temperature at said gas outlet necessary to maintain a desired humidity level in gas delivered to a patient;

algebraically add said selected destination temperature to said selected difference temperature by said electronic processor unit and generating a gas outlet temperature;

compare said generated gas outlet temperature and said destination temperature to said minimum required gas temperature at said gas outlet;

generate a low humidity signal if said generated gas outlet temperature or said destination temperature is less than said minimum required gas temperature at said gas outlet; and continuously generate said low humidity signal until a user changes said selected destination temperature and/or said selected difference temperature, such that said generated gas outlet temperature and said destination temperature is greater than or equal to said minimum required gas temperature at said gas outlet.

6. A humidifier system as claimed in claim 5 wherein said minimum required gas temperature at said gas outlet necessary to maintain a desired humidity level in gas delivered to a patient is a constant and said electronic controller is provided with memory means in which said minimum required gas temperature is stored.

7. A humidifier system as claimed in claim 6 wherein said electronic processor unit is provided with a warning light and/or aural signal indication means activated by said low humidity signal.

8. A humidifier system as claimed in claim 5 wherein said electronic processor unit is provided with a warning light and/or aural signal indication means activated by said low humidity signal.

* * * * *